United States Patent [19]

Cloutier

[11] Patent Number: 4,721,517
[45] Date of Patent: Jan. 26, 1988

[54] SAMPLING DEVICE FOR COLLECTING FUME

[75] Inventor: Yves Cloutier, Montreal, Canada

[73] Assignee: IRSST - Institut de recherche en santé et en sécurité du travail du Québec, Montreal, Canada

[21] Appl. No.: 23,116

[22] Filed: Mar. 6, 1987

[51] Int. Cl.⁴ ............................................. B01D 35/02
[52] U.S. Cl. ......................................... 55/270; 2/422; 73/863.23
[58] Field of Search .......... 55/270; 73/863.21, 863.23, 73/863.25, 863.83, 864.73; 2/422

[56] References Cited

U.S. PATENT DOCUMENTS

| | | | |
|---|---|---|---|
| 3,085,438 | 4/1963 | St. John et al. | 73/864.73 X |
| 3,686,835 | 8/1972 | Strange et al. | 55/270 |
| 3,748,905 | 7/1973 | Fletcher et al. | 73/863.25 |
| 4,178,794 | 12/1979 | Jugle et al. | 73/28 |
| 4,187,859 | 2/1980 | Allen et al. | 73/863.21 X |
| 4,202,212 | 5/1980 | Allen et al. | 55/270 X |
| 4,350,507 | 9/1982 | Greenough et al. | 55/270 |
| 4,455,881 | 6/1984 | Clark et al. | 73/863.21 |
| 4,594,903 | 6/1986 | Johnson | 73/863.83 |

OTHER PUBLICATIONS

Draft for Development, Methods for the Sampling and Analysis of Fume from Welding and Allied Processes, Part I, Particulate Matter BS1 DD54: 1977 British Standards Institution.
Jenkins, N. et al., Welding Fume: Sources, Characteristics, Control, Published by the Welding Institute, Abington, Cambridge, CBI Gal., 1981, vol. 1, Chap. 2 and 4.
Moreton, J., Welding Fume: A Critical Literature Review, published by The Welding Institute, Abington, Cambridge, CBI GAL, 1983, vol. 3, Chap. 2.
Goller J. W. and Paik N. W., General Electric Company, Erie, Pa., 16531 and Clayton Environmental Consultant Inc., Southfield, MI 48075., A Comparison of Iron Oxide Fume Inside and Outside of Welding Helmets., Am. Ind. Hyg. Assoc. J 46(2): 89–93, (1985).

Primary Examiner—Kathleen J. Prunner
Attorney, Agent, or Firm—Bacon & Thomas

[57] ABSTRACT

An improved sampling device for collecting at least part of air-borne particles in a workman's breathing zone. The device comprises a cassette provided with an inlet, an outlet and an air filter, a vacuum pump and a flexible tubing of determined length connecting the vacuum pump to the outlet of the cassette. In use, a portion of the air contained in the breathing zone of the workman is drawn through the filter and the particles collected thereon. This device is improved in that a deformable metallic tubing is positioned inside a portion of the flexible tubing or is positioned between a short length of a tubing connected to the outlet of the cassette and this flexible tubing. In addition, at least one fastener is provided for fixing the deformable metallic tubing and eventually the flexible tubing, to at least one strap intended to be tightened around a workman's head. This device is useful to position the air-intake of the cassette in the workman's breathing zone.

16 Claims, 7 Drawing Figures

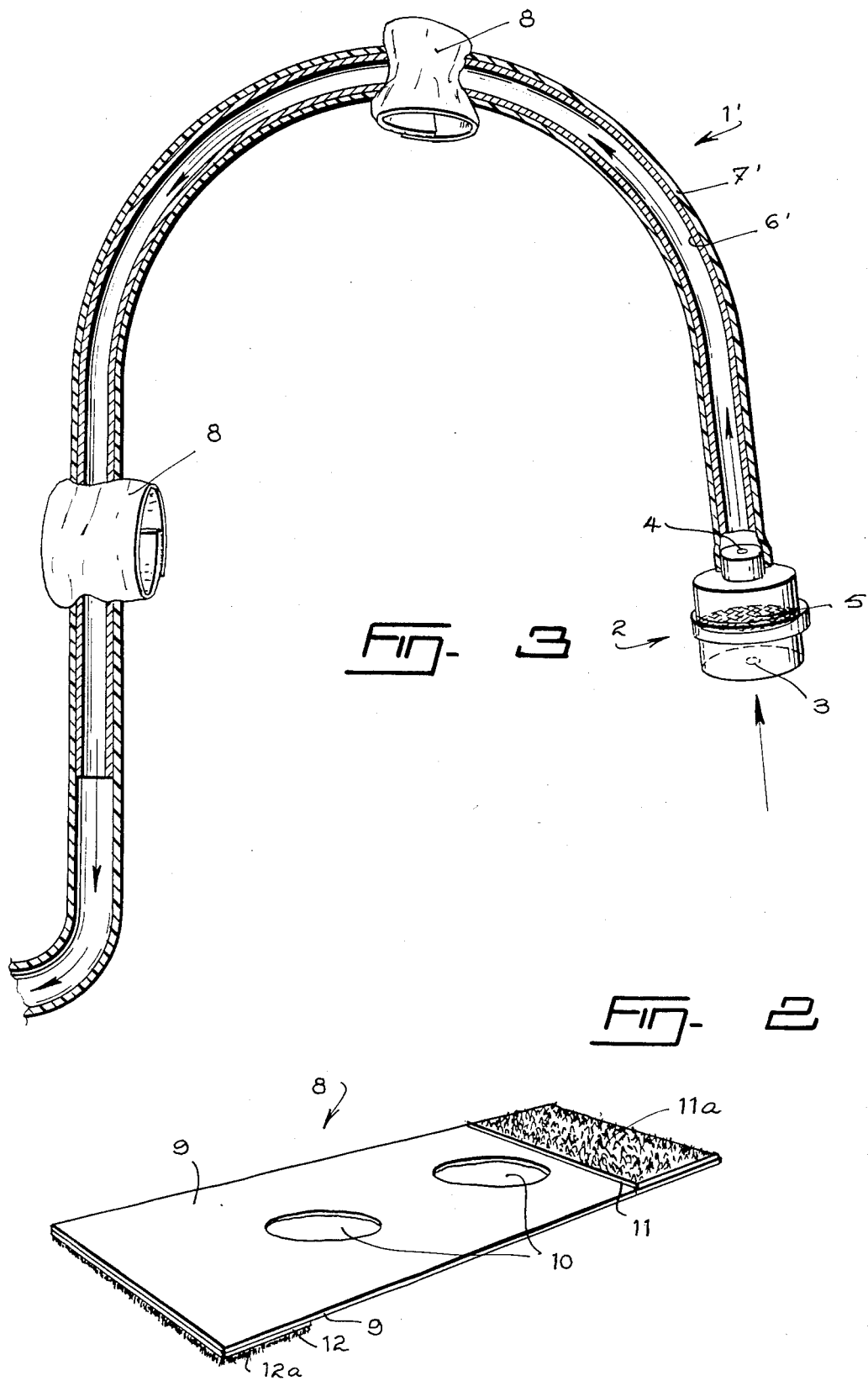

SAMPLING DEVICE FOR COLLECTING FUME

BACKGROUND OF THE INVENTION

1(a) Field of the Invention

The present invention relates to an improved device for measuring the amount of air-borne particles (i.e. fume) that may be inhaled by a workman (especially a welder).

1(b) Brief Description of the Prior Art

As evidenced by U.S. Pat. Nos. 4,178,794; 4,350,507 and 4,455,881, there presently exist various types of devices to be worn by a workman for measuring the amount of air-borne particles in a given area of work.

More particularly, U.S. Pat. No. 4,178,794 describes a device intended to be worn on a workman's chest. This device comprises a cassette provided with an inlet, an outlet and an air filter, the inlet of the cassette being connected to a cyclone which separates respirable and non-respirable air-borne particles, while the outlet of said cassette is connected to a portable vacuum pump.

U.S. Pat. No. 4,350,507 describes a device intended to be suspended either in front of a worker by use of straps passing around his neck and waist, or as an integral part of a helmet worn by said workman. This device comprises a housing defining an air passageway, an electric fan mounted in the passageway, a main filter located across the passageway to collect respirable air-borne particles and a prefilter located across the passageway upstream of the main filter, to collect non respirable air-borne particles.

U.S. Pat. No. 4,455,881 describes a device intended to be worn by a workman for sampling respirable aerosols contained in an atmosphere. This device comprises a selector capillary tube open at one end thereof to the atmosphere, a sampling capillary tube in fluid communication with the other end of the selector tube, and aspiration means in fluid communication with the sampling tube. The capillary tube may be wound on a small spool so that the entire sampling unit is rosette or button sized and can easily be worn by a workman on the lapel or in the manner of a badge.

All of these prior art devices are designed to allow measurements of air-borne particles that may be inhaled by a workman. Unfortunately, they are rather expensive and sophisticated. In addition, they fail to provide means for positioning the air intake within the breathing zone of the workman (i.e. at few centimeters of the workman's nose and mouth area). Also, when the air intake of the device is positioned inside a mask (e.g. in a welder's mask), the corresponding part of the device is fixed to said mask or makes an integral part of it. Therefore, reliable measurements are possible only when the workman wears his mask close to his face.

SUMMARY OF THE INVENTION

A first object of the present invention is to provide a device which overcomes the aforesaid drawbacks. More particularly, the first object of the invention is to provide an improved device of the above mentioned type, which is simple and inexpensive and is always positionable within the breathing zone of a workman, no matter whether this workman wears a mask or not.

Another object of the invention is to provide such an improved device which does not interfere with the activities of the workman and does not necessitate any modification to the equipment worn by said workman (especially the mask of a welder).

A further object of the invention is to provide a device which comprises a tubing portion fixed to the workman's head with straps, that contains or is made with such a deformable material (e.g. a deformable metal) that said tubing can be shaped with hands but cannot move by itself from its original position (i.e. within the workman's breathing zone) and swing like a pendulum to hit the workman's face.

According to a first embodiment of the invention, the sampling device for collecting at least a part of airborne particles in a workman's breathing zone, comprises a cassette provided with an inlet, an outlet and an air filter, a vacuum pump and a flexible tubing of determined length connecting the vacuum pump to the outlet of the cassette so that a portion of the air containing particles which is in the breathing zone, is drawn through the filter thereby collecting the particles thereon. In accordance with the invention, this device is improved in that a determined length of a deformable metallic tubing is positioned between one end of the flexible tubing and one end of a short tubing connected to the outlet of said cassette, and in that this deformable metallic tubing is fixed to at least one strap tightened around a workman's head, by means of at least one fastening means. Advantageously, the short tubing has resiliently deformable properties and may be a short portion of the aforesaid flexible tubing.

Preferably, two fastening means are used, one of them for fixing the deformable metallic tubing to a first strap intended to be tightened around a workman's head while the other is used for fixing the deformable metallic tubing to another strap connected to the first strap and intended to be positioned over the workman's head. These straps form advantageously an integral part of a helmet or mask worn by the workman. Each fastening means preferably consists of a strip of pliable material provided with two opposite ends, a pair of openings and a two-part fastener. Of course the openings are sized to be engaged by the deformable metallic tubing, and the strips of pliable material are sized to surround the straps intended to be either tightened or positionned around a workman's head. The two-part fastener is fixed to opposite ends of said strap of pliable material.

According to another embodiment of the invention, the sampling device for collecting air-borne particles in a workman's breathing zone, comprises a cassette provided with an inlet, an outlet and an air filter, a vacuum pump and a flexible tubing of determined length connecting the vacuum pump to the outlet of the cassette so that a portion of the air containing particles that are in the breathing zone, is drawn through the filter and thus collect thereon. In accordance with the invention, this device is improved in that a determined length of a deformable metallic tubing is positioned inside a portion of the length of a flexible tubing, and in that the portion of the flexible tubing containing the deformable metallic tubing is fixed to at least one strap that is intended to be tightened around the workman's head, by means of at least one fastening means.

Preferably, similarly to the first embodiment of the invention, two fastening means may be used to respectively fix the portion of flexible tubing containing the deformable metallic tubing, to a first strap intended to be tightened around a workman's head and another strap connected to the first strap and intended to be positioned over the workman's head.

In both embodiments, the deformable metallic tubing is preferably a copper or aluminum tubing eventually coated (externally and/or internally) with at least one thin layer of a protective material such as polyvinyl chloride (PVC).

In both embodiments, each strip of pliable material is preferably a strip of leather, and each two-part fastener is of the type consisting of a first small strip provided with a plurality of resiliently deformable hook-like projections and of a second small strip provided with a plurality of loop-like projections, each small strip being respectively fixed (e.g. with seams or by gluing) to one of both ends of the aforesaid pliable strip, and hook-like and loop-like projections being intended to be engaged one into the other. Advantageously, each two-part fastener is a VELCRO (trade mark) fastener.

The straps that are intended to be tightened and eventually positioned around the workman's head can form an integral part of a helmet (such as hard hat) eventually provided with a mask, or an integral part of a mask (such as a welder mask).

BRIEF DESCRIPTION OF THE DRAWINGS

The invention will be better understood with reference to the following non-restrictive description of preferred embodiments thereof, taken in connection with the accompanying drawings in which:

FIG. 1 is a perspective view of part of a device according to the invention where the deformable tubing and part of the flexible tubing are cut along their longitudinal axes to show a first preferred embodiment of the invention, FIG. 2 is a perspective view of the fastening means of the device of FIG. 1, FIG. 3 is a perspective view of part of a device according to the invention where the deformable tubing and part of the flexible tubing are cut along their longitudinal axes to show a second preferred embodiment of the invention.

DESCRIPTION OF PREFERRED EMBODIMENTS

Figure 7:
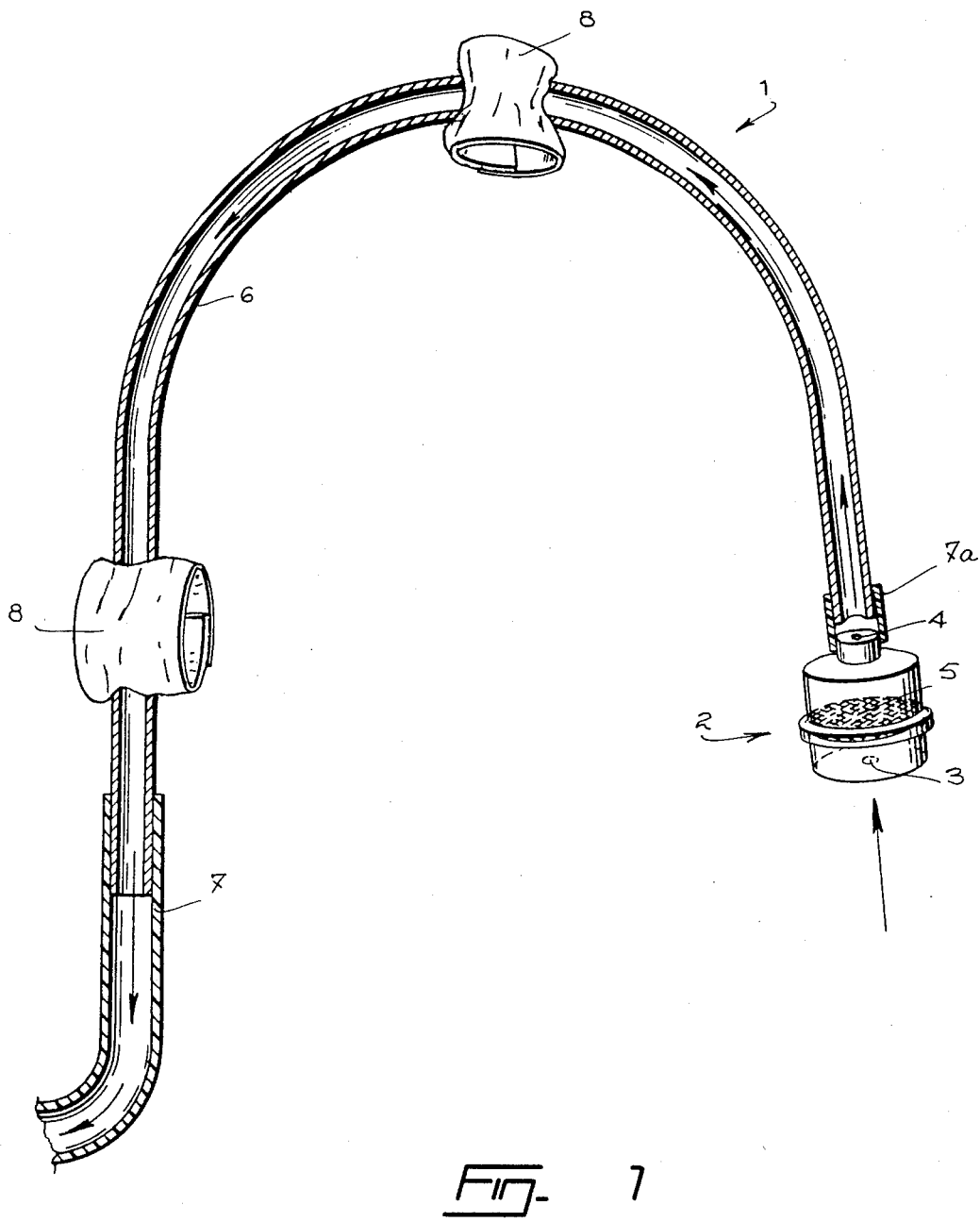
FIG. 7 is a perspective view of the device of FIG. 3, worn by a workman.

The improved device 1 according to the invention as shown in FIGS. 1, 2, 4 and 5 of the accompanying drawings, comprises a cassette 2 (especially a cylindrical plastic cassette having a 25 or 37 mm diameter) provided with an inlet 3 defining an air intake that has to be positioned within the breathing zone of a workman (see FIG. 4), a tubular outlet and an air filter 5 positioned inside the cassette between the inlet 3 and the outlet 4 so as a stream of air (see arrows) can pass through it. This filter 5 advantageously consists of a membrane of polyvinyl chloride (PVC) or of a membrane of cellulose esters, having a porosity of about 0.8 mm. The cassette 2 is advantageously provided with means for supporting the filter 5 and made of two parts engageable one into the other to allow an easy positioning or recovering of the filter 5 for analysis purposes.

Advantageously, one part of the cassette 2 is provided with a circular edge and an outer cylindrical surface, and the other part is provided with a circular shoulder and an inner cylindrical surface. Eventually, both aforesaid surfaces are threaded. When said parts are engaged one into the other or screwed together by engagement of their corresponding threaded cylindrical surfaces, the filter 5 is pinched between said edge and shoulder.

Figure 5:
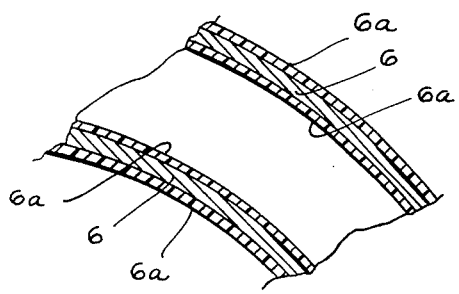
FIG. 5 is a partial view of a portion of the deformable tubing of the device of FIG. 1 showing an alternative embodiment of the invention.

The device 1 also comprises a metallic deformable tubing 6 (especially a copper or aluminum tubing of 0.25 in. external diameter (length: about 40–45 cm)). Advantageously, as shown in FIG. 5, the deformable tubing 6 has its outer and inner cylindrical surfaces coated with a thin layer 6a of a protective material such as PVC. More particularly, these thin layers 6a protect the metallic tubing from corrosive agents.

The device 1 also comprises a tubing 7a of short length (especially a tubing made of TYGON (trade mark) and having a 0.25 in. internal diameter and a 0.375 in. external diameter (length: 1 to 3 cm)) whose one end thereof is forced over one of both free ends of the deformable tubing 6 in order to define an airtight connection, while the opposite end of this tubing 7a is forced over the cylindrical outlet 4 to form an airtight connection. Advantageously, the outer diameter of the outlet 4 and of the tubing 6 is slightly greater than the inner diameter of the tubing 7a to improve the airtight connection.

Figure 4:
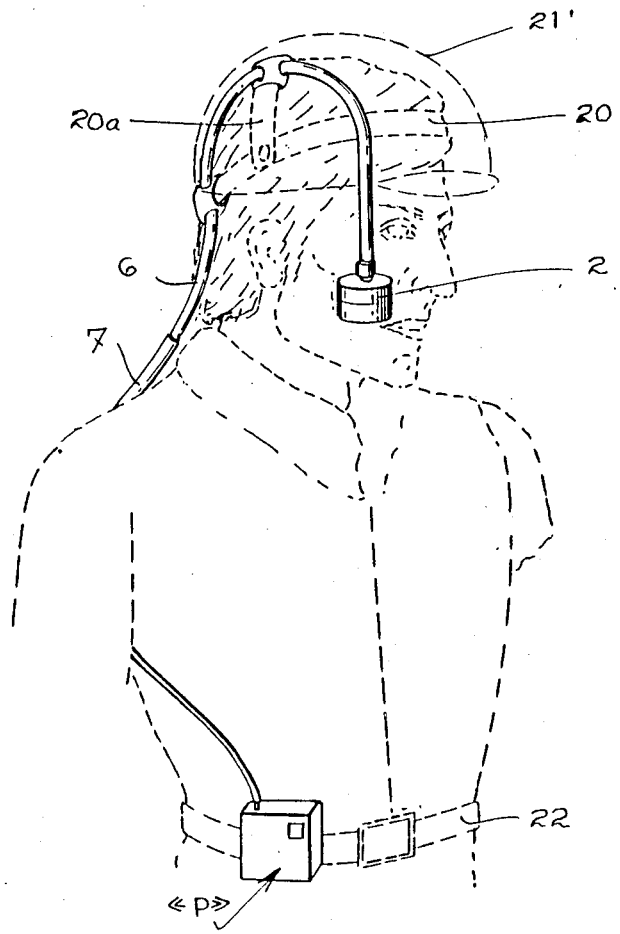
FIG. 4 is a perspective view of the device of FIG. 1, worn by a workman.

The device 1 also comprises a flexible tubing 7 (especially a tubing made of TYGON (trade mark) and having a 0.25 in. internal diameter and a 0.375 in. external diameter (length: about 1 meter)) whose one end thereof is forced over the free end of the deformable tubing 6 in order to define an airtight connection, while the opposite end is forced over a cylindrical tubular inlet of a portable vacuum pump "P" (see FIG. 4).

The pump "P" is advantageously of the type provided with rechargeable cells and has to be operable for the entire period of sampling (e.g. 8 hours). This pump must be as light as possible to not interfere with the work of the workman and has to provide a steady and regular stream of air (without pulses) through the filter during the entire period of sampling, advantageously with a flow rate of $1.5\pm5\%$ liter per minute (1. $mn^{-1}$).

The device 1 also comprises two fastening means 8 (see FIG. 2). Each means 8 consists of one strip 9 made of leather and provided with two openings 10 through which the deformable tubing 6 is intended to be inserted, and a two part fastener. This two part fastener is of the type consisting of a first small strip 11 provided with a plurality of resiliently deformable hook-like projections 11a, and of a second small strip 12 provided with a plurality of loop-like projections 12a, said small strips 11 and 12 being respectively fixed (e.g. with seams or by gluing) to one of said opposite ends of the strip 9, and projections 11a and 12a being intended to be engaged one into the other. Preferably, the two part fastener is a VELCRO (trade mark) fastener whose both parts are respectively fixed to opposite ends of the strap of leather.

Also, in accordance with another embodiment, the improved device 1' according to the invention as shown in FIGS. 2, 3, 6 and 7 of the accompanying drawings, comprises a cassette 2 identical to the one shown in FIG. 1.

The device 1' also comprises a flexible tubing 7' (especially a tubing made of TYGON (Trade mark) and having a 0.25 in. internal diameter, a 0.375 in. external diameter and a length of 130–140 cm), whose one end thereof is forced over the cylindrical outlet 4 to form an air tight connection while the opposite end is forced over a tubular inlet of a portable vacuum pump "P" (shown in FIG. 7) identical to the one described hereinabove. The outlet 4 and the inlet of the pump "P" have preferably an outer diameter slightly greater than the inner diameter of the tubing 7' to improve the airtight connection.

The device 1' also comprises a deformable metallic tubing 6' (especially a copper or aluminum tubing of 0.25 in. external diameter, length 40–45 cm), positioned inside the flexible tubing 7'. One end of said tubing 6' is positioned at 1 to 2 centimeters from the end of the tubing 7' that is forced over the outlet 4. The deformable tubing 6' is advantageously introduced inside the tubing 7' after having been coated with talc powder (lubricant). The device 1' also comprises two fastening means 8 (see FIG. 2) that are identical to the ones used with the device of FIG. 1.

Figure 6:
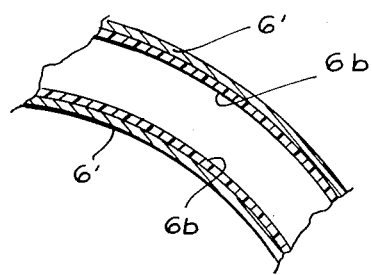
FIG. 6 is a partial view of a portion of the deformable tubing of the device of FIG. 3, showing another alternative embodiment of the invention.
Figure 7:
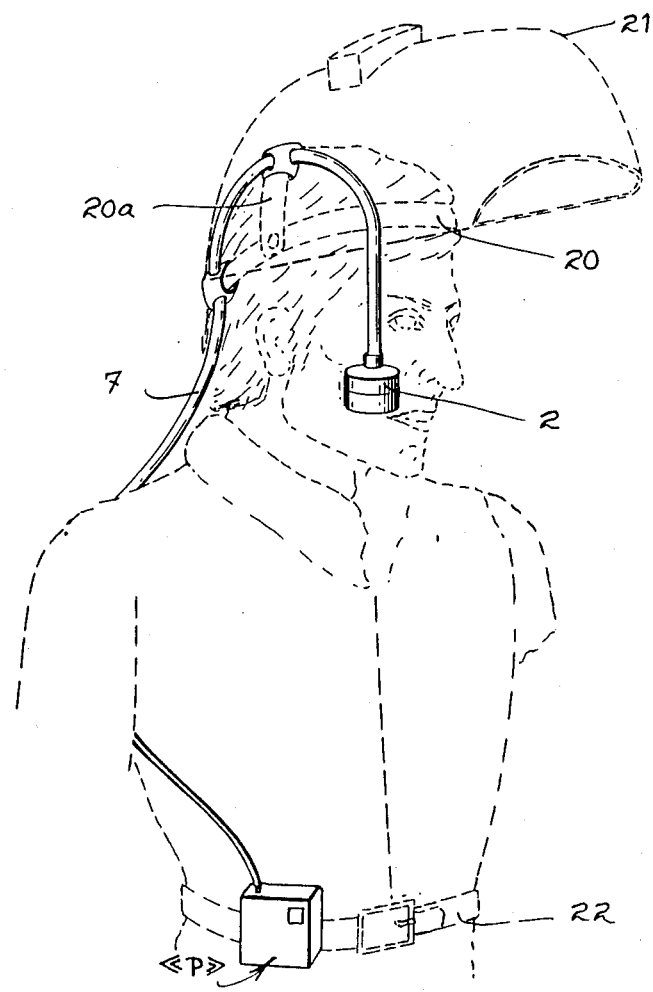

Advantageously, as shown in FIG. 6, the deformable tubing 6' has its inner cylindrical surface coated with a thin layer 6b of a protective material such as PVC. More particularly, this layer 6b protects the tubing 6' from corrosive agents.

To use a device as shown in FIG. 3, a workman such as a welder (see FIG. 7) has to carry out the following steps:

(i) Disengage both parts of the cassette 2, one of said part being provided with a circular edge and an eventually threaded, outer cylindrical surface, and the other part being provided with a circular shoulder and an eventually threaded, inner cylindrical surface, said surfaces or threaded surfaces being intended to fit one into the other.

(ii) Position between the edge and shoulder, a filter 5 of appropriate size and then reengage or rescrew said parts of the cassette 2 till said edge and shoulder pinch the filter 5.

(iii) Slide the deformable tubing 6' completely inside a flexible tubing 7' (after having eventually coated the outer cylindrical surface of said tubing 6' with talc powder) till one end of the tubing 6' be at 1 to 2 cm from one end of the tubing 7'.

(iv) Pass the portion of flexible tubing 7' that contains the deformable tubing 6', through openings 10 of two strips 9.

(v) Force the end of the flexible tubing 7' (where the deformable tubing 6' is positioned) over the cylindrical outlet 4 of the cassette 2, the other end of the tubing 7' being forced over the cylindrical inlet of a portable vacuum pump "P".

(vi) Disengage hook-like projections 11a from loop-like projections 12a, pass the strips 9 respectively around the strap 20 and the strap 20a of his mask 21 and then engage said hook-like projections 11a in loop-like projections 12a, to thus fix the portion of flexible tubing 7' (which contains the deformable tubing 6') to the straps 20 and 20a of his mask 21; and then fixing in a conventional manner the pump "P" to his belt 22. Advantageously, the pump is fixed to the workman's belt with a clip making an internal part of said pump.

(vii) Deform and slide with his hands the portion of flexible tubing that contains the tubing 6', in order to position the air intake (i.e. inlet 3) of the cassette 2 in his breathing zone (e.g. <10 cm around his nose-mouth area). The cassette 2 is not allowed to swing like a pendulum because of the deformable metallic tubing; and (viii) Switch on the pump "P", do his professional work for a determined period of time and then switch off the pump "P", remove the cassette 2 and give it to a technician for analysis purposes.

Of course, to use a device as shown in FIG. 1, a workman who wears a hard hat 21' (see FIG. 4) has to carry out the same steps than those mentioned for the device of FIG. 3, except that step (iii) is replaced by a step where one end of the flexible tubing 7 is forced over one end of the deformable tubing 6, that in step (iv) only the deformable tubing is passed through the openings 10 of the strips 9 and that in step (v) one end of a tubing 7a is forced over the cylindrical outlet 4 of the cassette 2, the other end of the tubing 7a is forced over the remaining end of the deformable tubing 6, and the other end of the flexible tubing 7 is forced over the cylindrical inlet of a portable vacuum pump <<P>>.

To dismount the devices of FIG. 1 or 3, a workman only has to carry out the appropriate above mentioned steps in a reverse way.

What is claimed is:

1. A sampling device for collecting at least part of air-borne particles in a workman's breathing zone, said device comprising a cassette provided with an inlet, an outlet and an air filter, a vacuum pump and a flexible tubing of determined length connecting the vacuum pump to the outlet of the cassette so that a portion of the air-borne particles in said breathing zone, is drawn through said filter and is collected thereon, wherein:

a deformable metallic tubing is positioned between one end of the flexible tubing and one end of a short tubing connected to the outlet of the cassette, and at least one fastening means is provided for fixing the deformable metallic tubing to at least one strap intended to be tightened around a workman's head.

2. A device according to claim 1, wherein the deformable metallic tubing is a copper or aluminum tubing.

3. A device according to claim 2, wherein the deformable metallic tubing is coated with at least one layer of a protective material.

4. A device according to claim 3, wherein said protective material is polyvinyl chloride.

5. A device according to claim 1, wherein one fastening means is provided for fixing the deformable metallic tubing to a first strap intended to be tightened around a workman's head, a further fastening means is provided for fixing the deformable metallic tubing to a second strap connected to the first one and positioned over the workman's head, said straps forming part of a helmet worn by said workman, each fastening means consisting of a strip of pliable material provided with two opposite ends, a pair of openings and a two-part fastener fixed to said opposite ends, said pair of openings being sized to be engaged by the deformable metallic tubing, said strip of pliable material being sized to surround one of said straps of the helmet.

6. A device according to claim 5, wherein the strip of pliable material is made of leather and the two-part fastener is of the type consisting of a first small strip provided with a plurality of resiliently deformable hook-like projections, and of a second small strip provided with a plurality of loop-like projections, each of said small strips being respectively fixed to one of said opposite ends of the strip of pliable material, and said hook-like and loop-like projections being intended to be engaged one into the other.

7. A device according to claim 1, wherein one fastening means is provided for fixing the metallic deformable tubing to a first strap intended to be tightened around a workman's head, a further fastening means is provided for fixing the deformable metallic tubing to a second strap connected to the first strap and intended to be positioned over the workman's head, said straps forming part of a mask worn by said workman, each fastening means consisting of a strip of pliable material provided with two opposite ends, a pair of openings and a two-part fastener fixed to said opposite ends, said pair of openings being sized to be engaged by the deformable metallic tubing, said strip of pliable material being sized to surround one of said straps of the mask.

8. A device according to claim 7, wherein the mask is a welder mask, the strip of pliable material is made of leather and the two-part fastener is of the type consisting of a first small strip provided with a plurality of resiliently deformable hook-like projections, and of a second small strip provided with a plurality of loop-like projections, each of said small strips being respectively fixed to one of said opposite ends of the strip of pliable material, and said hook-like and loop-like projections being intended to be engaged one into the other.

9. A sampling device for collecting air-borne particles in a workman's breathing zone, said device comprising a cassette provided with an inlet, an outlet and an air filter, a vacuum pump and a flexible tubing of determined length connecting the vacuum pump to the outlet of the cassette so that a portion of the air born particles in said breathing zone, is drawn through said filter and is collected thereon, wherein:
a deformable metallic tubing is positioned inside a portion of the length of the flexible tubing, and
at least one fastening means is provided for fixing the portion of the flexible tubing containing said deformable metallic tubing, to at least one strap intended to be tightened around the workman's head.

10. A device according to claim 9, wherein the deformable metallic tubing is a copper or aluminum tubing.

11. A device according to claim 10, wherein the deformable metallic tubing is coated with at least one layer of protective material.

12. A device according to claim 11, wherein said protective material is polyvinyl chloride.

13. A device according to claim 9, wherein one fastening means is provided for fixing the portion of flexible tubing containing the deformable metallic tubing to a first strap intended to be tightened around a workman's head, a further fastening means is provided for fixing the deformable metallic tubing to a second strap connected to the first one and intended to be positioned over the workman's head, said straps forming part of a helmet worn by said workman, each fastening means consisting of a strip of pliable material provided with two opposite ends, a pair of openings and a two-part fastener fixed to said opposite ends, said pair of openings being sized to be engaged by the portion of flexible tubing containing the deformable metallic tubing, said strip of pliable material being sized to surround one of said straps of the helmet.

14. A device according to claim 13, wherein the strip of plible material is made of leather and the two-part fastener is of the type consisting of a first small strip provided with a plurality of resiliently deformable hook-like projections, and of a second small strip provided with a plurality of loop-like projections, each of said small strips being respectively fixed to one of said opposite ends of said strip of pliable material, and said hook-like and loop-like projections being intended to be engaged one into the other.

15. A device according to claim 9, wherein one fastening means is provided for fixing the portion of flexible tubing containing the deformable metallic tubing to a first strap intended to be tightened around a workman's head, a further fastening means is provided for fixing the deformable metallic tubing to a second strap connected to the first strap and intended to be positioned over the workman's head, said straps forming part of a mask worn by said workman, each fastening means consisting of a strip of pliable material provided with two opposite ends, a pair of openings and a two-part fastener fixed to said opposite ends, said pair of openings being sized to be engaged by the portion of flexible tubing containing the deformable metallic tubing, said strip of pliable material being sized to surround one of said straps of the mask.

16. A device according to claim 15, wherein the strip of pliable material is made of leather and the two-part fastener is of the type consisting of a first small strip provided with a plurality of resiliently deformable hook-like projections, and of a second small strip provided with a plurality of loop-like projections, each of said small strips being respectively fixed to one of said opposite ends of said strip of pliable material, and said hook-like and loop-like projections being intended to be engaged one into the other.

* * * * *